United States Patent
Doyle

[19]

[11] Patent Number: 5,890,891
[45] Date of Patent: Apr. 6, 1999

[54] REVERSE PULL, EXTRAORAL DENTAL ASSEMBLY WITH HEAD AND BODY SUPPORTS AND CHIN STOP

[75] Inventor: Walter A. Doyle, Lexington, Ky.

[73] Assignee: RMO, Inc., Denver, Colo.

[21] Appl. No.: 79,904

[22] Filed: May 15, 1998

[51] Int. Cl.⁶ ...................................................... A61C 3/00
[52] U.S. Cl. .................................................................. 433/5
[58] Field of Search .................................... 433/5, 18, 24; 128/97.1, 857, 859, 861; 602/17, 18

[56] References Cited

U.S. PATENT DOCUMENTS

| | | | |
|---|---|---|---|
| 2,151,458 | 3/1939 | Allen ......................................... | 128/87 |
| 2,334,894 | 11/1943 | Atkinson . | |
| 2,681,058 | 6/1954 | Mathues . | |
| 3,401,457 | 9/1968 | Hickham . | |
| 4,375,962 | 3/1983 | DeWoskin ................................... | 433/5 |
| 4,951,655 | 8/1990 | MacMillan et al. . | |
| 4,988,291 | 1/1991 | Grummons ................................... | 433/5 |
| 5,062,415 | 11/1991 | Weatherby et al. . | |
| 5,810,583 | 9/1998 | Doyle ......................................... | 433/5 |

FOREIGN PATENT DOCUMENTS 28 03 560 A1   8/1979   Germany .

OTHER PUBLICATIONS

Advertisement, "Heavy Force Face Mask", Dr. Henri Petit, Great Lakes Orthodontic Laboratories Inc., Buffalo, N.Y. 14216.

*Primary Examiner*—Ralph A. Lewis
*Attorney, Agent, or Firm*—Sheridan Ross P.C.

[57] ABSTRACT

A reverse pull, extraoral dental assembly having at least one head support, at least one body support (e.g., disposed outside of the head region of the dental patient) and at least one chin stop is provided. The head support, body support, and chin stop are interconnected by a brace assembly which is displaced outwardly from the frontal region of the dental patient. One and typically two elastics or other appropriate treatment force generating/transfer members extend from the brace assembly to engage one or more of the dental patient's teeth in the upper and/or lower arch to apply a generally mesially directed treatment force thereto, and/or to engage a device which is directly associated with dental patient bone (e.g., an implant or onplant). The chin support provides a counterforce to any upward force exerted by the assembly thus preventing an upward movement of the assembly.

29 Claims, 7 Drawing Sheets

5,890,891

REVERSE PULL, EXTRAORAL DENTAL ASSEMBLY WITH HEAD AND BODY SUPPORTS AND CHIN STOP

This application incorporates by reference herein U.S. Pat. No. 5,810,583, filed on Feb. 28, 1996, in its entirety.

FIELD OF THE INVENTION

The present invention generally relates to applying generally mesially directed forces to a patient, for instance to treat many types of malocclusions requiring orthopedic advancement of the maxilla and/or mandible or advancement of the dentition and, more particularly, to a reverse pull, extraoral dental assembly which includes at least one head support, at least one body support interconnected by a brace assembly for "anchoring" a generally mesially directed treatment force exerted on the patient (e.g., one or more upper teeth and/or lower teeth of a patient, directly on patient bone), and a chin stop to prevent the upward movement of the brace assembly.

BACKGROUND OF THE INVENTION

One type of malocclusion is a Class III which often times involves a maxillary deficiency. A Class III malocclusion is a condition in which the chin of an individual appears to protrude forwardly a disproportionate amount. Class III malocclusions may be due to excessive mandibular growth and/or maxillary deficiency. One method for treating a Class III malocclusion involving a retracted maxilla is to exert a generally mesially directed force on the bony structures of the lower face by engaging the upper arch of the orthodontic patient. These types of force stimulate bone growth to advance the maxilla mesially and/or orthodontically advance the patient's dentition.

Another type of malocclusion is a Class II malocclusion. A Class II malocclusion exhibits a rearward displaced chin or generally underdeveloped jaw. Particularly in younger patients, this type of malocclusion responds well to generally mesially-directed treatment forces.

The above-noted types of mesially-directed forces are typically applied using what may be characterized as a reverse pull assembly. Known reverse pull assemblies allow for the exertion of the generally mesially-directed force on the patient's upper arch or lower arch by providing a plurality of supports on the patient's facial or head region and by including structure which is outwardly displaced from the patient's face to provide a mounting for elastics or other treatment force generating members. These elastics extend from their mounting on the reverse pull assembly under tension and engage the patient's upper or lower arch. In the case where a rigid arch wire or the like is interconnected with the patient's upper or lower teeth, a pair of elastics are typically used to engage opposite sides of the arch undergoing treatment (e.g,. by engaging hooked appliances indirectly attached to bands on the patient's teeth). The tensioned elastics thereby apply a symmetrical, generally mesially-directed force on the patient's arch undergoing treatment to attempt to achieve the noted objectives, while the corresponding generally distally directed forces are exerted on the patient at the various facial or head supports.

SUMMARY OF THE INVENTION

The present invention generally relates to a reverse pull, extraoral dental assembly which utilizes at least one frontal support on the facial region of the dental patient, at least one frontal support on the body region or outside of the facial region of the dental patient, and at least one chin stop to prevent the upward movement of the brace assembly. At least one of the frontal supports on the facial region of the dental patient is interconnected with at least one chin stop and at least one of the frontal supports disposed outside of the facial region of the dental patient by a brace assembly. The brace assembly is displaced outwardly from the "front" of the dental patient and includes at least one appropriate mount. Elastics or other appropriate force generating/transmitting members engage a mount and extend into the patient's mouth, for instance to engage one or more of the patient's teeth to apply the generally mesially-directed force to the teeth which may be used to affect movement of the dentition and/or to stimulate bone growth. The assembly may also be connected directly to the bone of the upper and/or lower jaws with implants in the bone or "onplants" which are on the bone and under the periosteum, and therefore capable of applying these forces more directly to the bone. Other means include an acrylic palatal appliance or other palate or mandible-engaging functional appliances. That is, the present invention and its ability to transmit generally mesially-directed forces to a dental patient may be used to affect a pure orthodontic treatment, a pure orthopedic treatment, and for combinations thereof.

In one embodiment, at least one frontal support is provided for engaging a portion of the dental patient's forehead and is disposed substantially on or symmetrically relative to the dental patient's vertical midline (i.e., a vertical reference plane which bisects the dental patient). At least one other frontal support is provided for engaging a frontal portion of the dental patient's body, such as at or near the sternum region, and is also disposed substantially on or symmetrically relative to the dental patient's vertical midline. And at least one chin stop is provided for engaging a portion of the dental patient's chin to counteract any upward force generated by the brace assembly. The brace assembly is also thereby substantially coplanar with the dental patient's vertical midline. The facial and body supports and the chin stop may be a single support or, alternatively, two or more displaced supports (e.g., disposed symmetrically relative to the noted vertical midline).

Various features which may be incorporated in the reverse pull, extraoral dental assembly of the present invention will be discussed in relation to the above-described embodiment. For instance, the brace assembly may include upper and lower braces which are telescopingly interconnected to accommodate bowing-like movements of the dental patient's head. Relatedly, the brace assembly may be interconnected with the frontal supports in a manner which does not significantly impede other types of movements of the dental patient's head (e.g., by pivotally interconnecting the two ends of the brace assembly with the two frontal supports and also allowing the brace assembly to swivel relative to the same), but which yet still maintains the brace assembly in a position which allows for the continued application of a generally symmetrical force to the dental patient during treatment (e.g., to keep the brace assembly on the patient's vertical midline). Moreover, the positioning of the mount(s) on the brace assembly can be adjusted to accommodate physical differences between dental patients and/or to allow for changing the orientation of the vector of the forces being applied to the dental patient undergoing treatment (e.g., to allow an attending orthodontist to exert a more "downwardly" directed mesial force on the dental patient's upper arch than is typically utilized). When a downwardly directed mesial force is applied, the assembly has a tendency to creep upwardly until the downward force vector is eliminated. In order to prevent such upward creep, the assembly can include a chin stop assembly. The chin stop assembly is designed to engage the dental patient under the chin in order to minimize undesirable upward creep of the assembly.

DETAILED DESCRIPTION OF THE INVENTION

Figure 1:
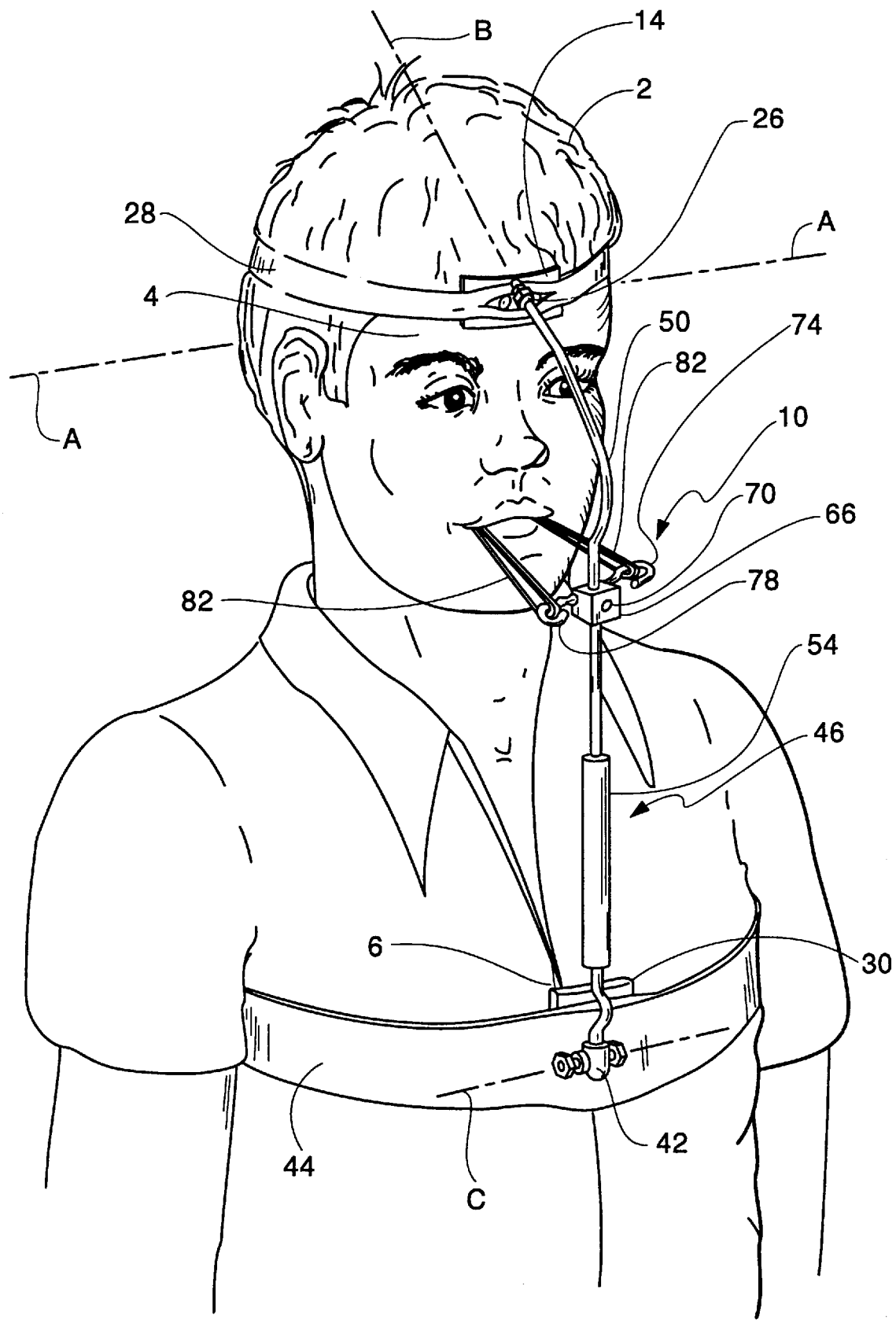
FIG. 1 is a perspective view of one embodiment of a reverse pull, extraoral dental assembly, in accordance with principles of the present invention, being worn by a dental patient.

The present invention provides an apparatus and a method for transmitting generally mesially-directed forces to a dental patient to affect a pure orthodontic treatment, a pure orthopedic treatment, or a combinations thereof.

A reverse-pull, extraoral dental assembly of the present invention comprises a first means for engaging a portion of the dental patient's facial region. The first means can be any device for engaging a portion of the dental patient's facial region. For example, the first means can include an upper support which engages the forehead of the dental patient.

The assembly of the present invention can comprise a second means for engaging a portion of the dental patient's body spaced from the patient's head. The second means can be any device for engaging a portion of the dental patient's body spaced from the patient's head. For example, the second means can include a lower support which engages the sternum region of the dental patient.

The lower and upper support can be made from a material including, but not limited to, a metal (e.g., stainless steel or perforated steel), plastic, wood, hard rubber, foam, fabric, and combinations thereof. The lower and upper support can also include padding for comfortably engaging the dental patient.

The assembly can also comprise a third means for interconnecting the first and the second means. The third means can be any device which allows interconnection of the first and the second means. The third means is generally displaced outwardly from a frontal region of the dental patient.

The assembly can have a fourth means which can be interconnectable with the third means for exerting at least a mesially directed force on at least one of the patient's lower jaw (i.e., mandible), the patient's maxilla, and a tooth of the patient. The fourth means can be any device which can be interconnectable with the third means for exerting at least a mesially directed force on at least one of the patient's lower jaw, the patient's maxilla, and a tooth of the patient. For example, the fourth means can be an elastic member, a telescoping metal, plastic or wood member, or a combination thereof.

The assembly can also have a fifth means, interconnectable with the third means, for providing a counter force to any downward force exerted by the fourth means. The fifth means can be any device which can be interconnectable with the third means and provides a counter force to any downward force exerted by the fourth means. For example, the fifth means can include a chin stop assembly which prevents the assembly from creeping upward.

The present invention will be further described in detail in relation to the accompanying drawings which assist in illustrating its various pertinent features. A reverse pull, extraoral dental assembly 10 is disclosed in FIGS. 1–6 which may be used for a variety of treatments which require the application of a generally mesially-directed treatment force to a dental patient (e.g., typical malocclusions such as Class II and Class III malocclusions). The assembly 10 accommodates for the application of this force at an angle relative to the occlusal plane. The assembly 10 may be used for orthopedic treatments or treatments which involve moving and/or stimulating the growth of bone, and/or for orthodontic treatments which involve the movement of the dentition (e.g., the assembly 10 may be used to provide a pure orthodontic treatment, a pure orthopedic treatment, or a combination thereof).

The assembly 10 may be interconnected with one or more teeth of the upper arch of the orthodontic dental patient 2, one or more teeth of the lower arch, and/or one or more teeth of both arches simultaneously to affect the desired treatment, and/or bone engaging means as described above. This type of interconnection may be used to stimulate bone growth and/or affect movement of the dentition. That is, the assembly 10 may be interconnected with the dental patient in this manner to affect a pure orthopedic treatment, a pure orthodontic treatment, and to simultaneously affect an orthopedic treatment and an orthodontic treatment. The assembly 10 may also be connected directly to the bone of the upper or lower jaws with implants in the bone or "onplants" which are on the bone and under the periosteum, and therefore capable of applying these forces more directly to the bone. Other means for establishing an interconnection include an acrylic palatal appliance or other palate or mandible-engaging functional appliances. The assembly 10 may also be used in a variety of types of treatments, such as for treating the above-noted malocclusions, for distraction, i.e., the orthopedic pulling of broken bones to encourage growth during healing, and for use during sagittal palatal expansion.

The assembly 10 includes an upper support 14 which engages the forehead 4 of the dental patient 2 and a lower support 30 which engages the body of the dental patient 2, typically in the upper sternum region 6. The upper support 14 and the lower support 30 are interconnected by a brace assembly 46 which is disposed outwardly from the frontal region of the dental patient 2. As such, elastics 82 or other force generating members may extend from the brace assembly 46 to the dental patient 2 to apply the above-described type of generally mesially-directed orthopedic and/or orthodontic treatment force. The lower support 30 is illustrated as interfacing with a more "upper portion" of the sternum 6, such as between the main body of the sternum and the manubrium which is a more preferred position. It will be appreciated that the lower support 30 could interface with a "lower" portion of the sternum as well, although this is not preferred.

Figure 3:
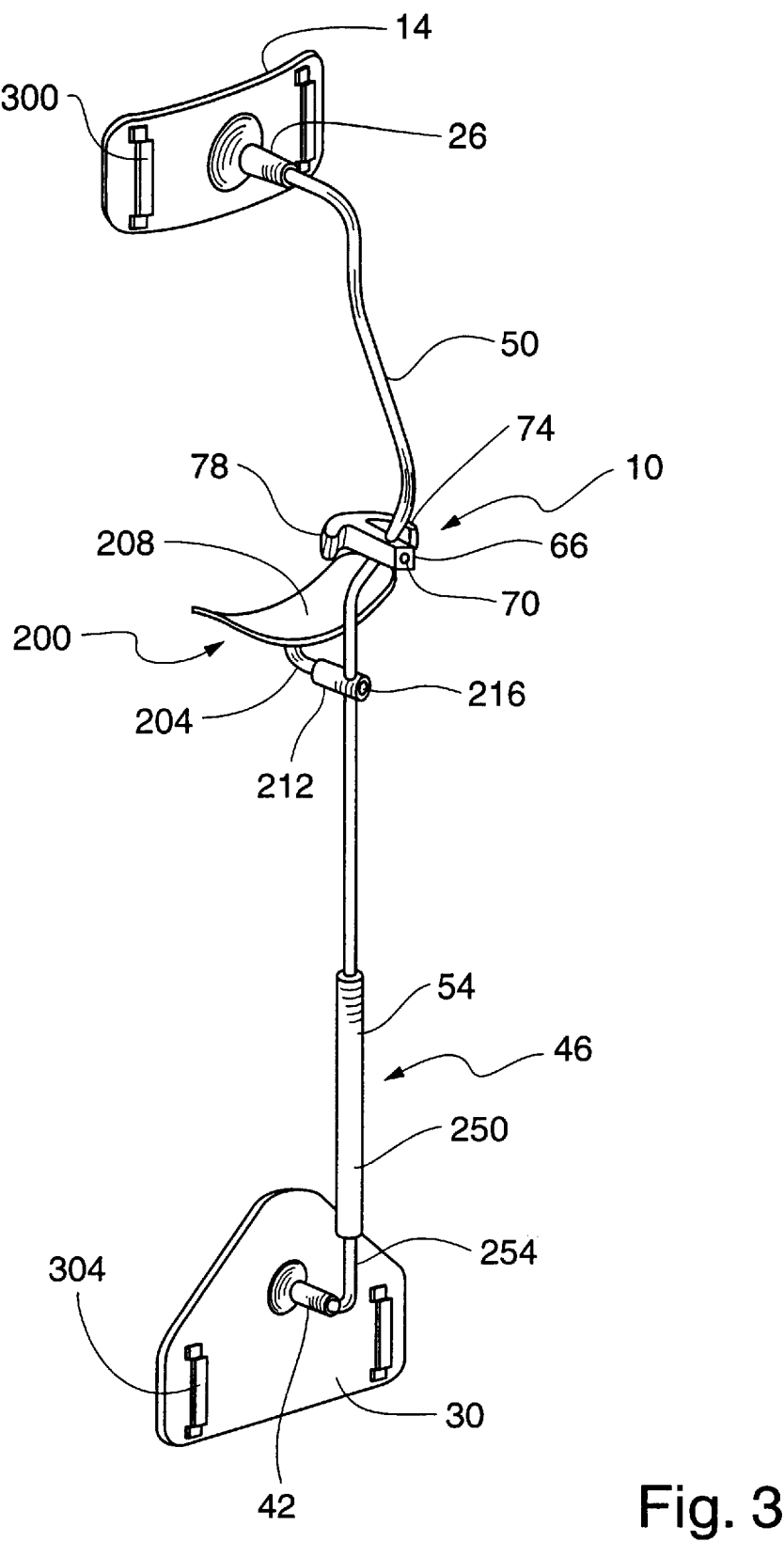
FIG. 3 is a view of another embodiment of a reverse pull, extraoral dental assembly having a chin stop assembly.
Figure 4:
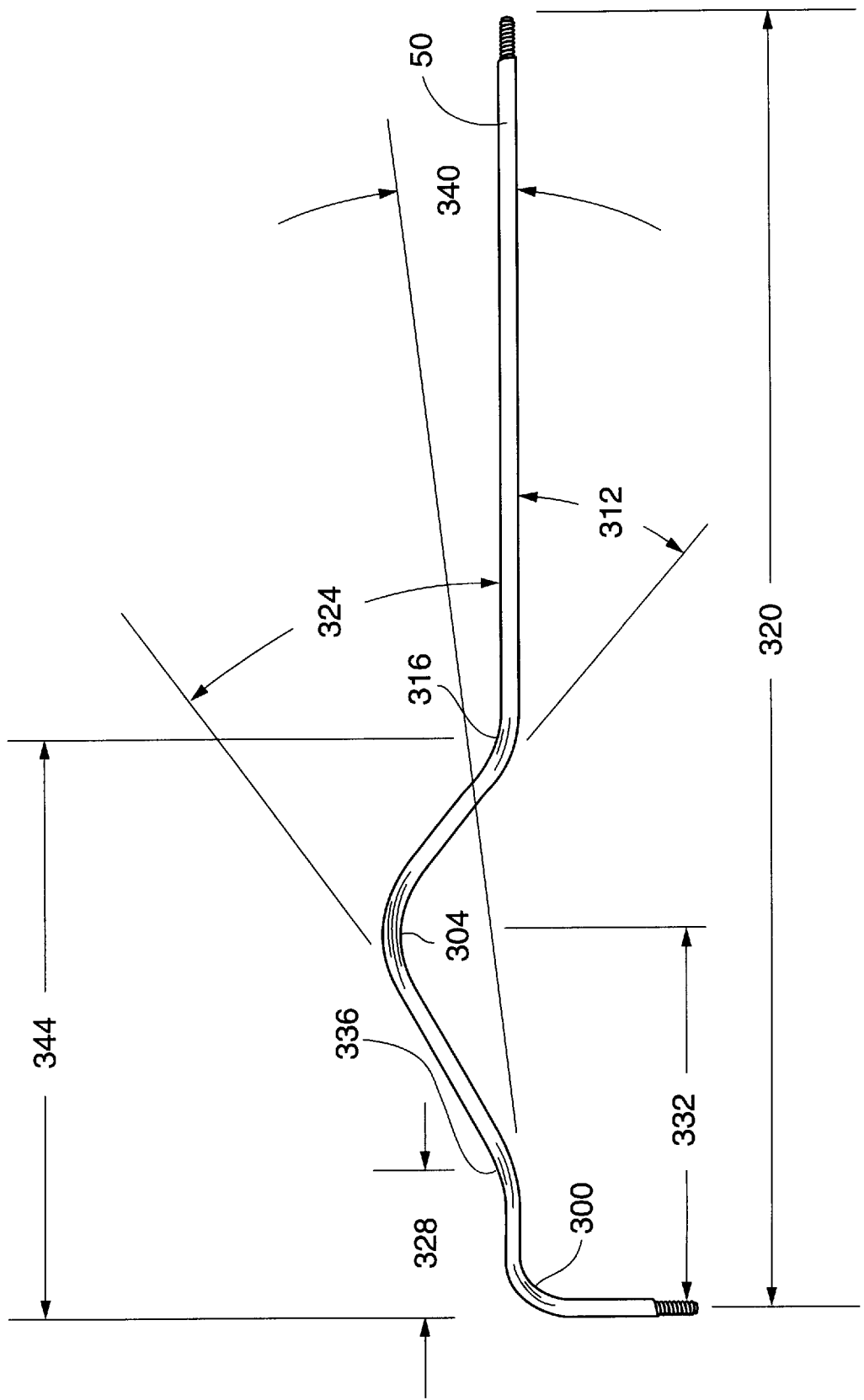
FIG. 4 is a detailed view of the upper brace 50.

The upper support 14 is generally rigid and may be custom contoured and padded for providing a comfortable interface with the forehead 4 of the dental patient 2. An upper strap assembly 28 (e.g., a pair of velcro straps) is interconnected with the upper support 14 to secure the upper support 14 to the dental patient 2, typically by passing the upper strap assembly 28 about the head of the dental patient 2. The upper support 14 can also include one or more strap loops 300 as shown in FIG. 3. The strap loop 300 provides a more secure attachment of the upper support 14 to the forehead of the dental patient by reducing or eliminating the movement of the upper support 14 when the dental patient's head is turned or moved. The upper support 14 is movably interconnected with the brace assembly 46, specifically the upper brace 50, by an upper connector 26. Preferably, the upper connector 26 is interconnected to the upper support by a ball-type joint or any other connection mechanism which allows the upper connector 26 to pivot about the upper support 14. A connection mechanism such as a ball-type joint allows the upper connector 26 to pivot about the axis A of the upper support 14 (e.g., a generally vertical pivoting action). And it allows the upper connector 26 to swivel about the axis B of the upper support 14 (e.g., about an axis generally normal to the forehead 4).

The lower support 30 is generally rigid and may be contoured and padded for providing a comfortable interface with the sternum region 6 of the dental patient 2. A lower strap assembly 44 (e.g., a pair of velcro straps) is interconnected with the lower support 30 to secure the lower support 30 to the dental patient 2, typically by passing the lower strap assembly 44 about the body of the dental patient 2. As shown in FIG. 3, similar to the upper support 14, the lower support 30 can also have one or more strap loop 304 to reduce or eliminate the movement of the lower support. The lower strap assembly 44 can also include a pair of shoulder strap 400 which is interconnected to the lower strap assembly 44. Placement of the shoulder strap 400 on the dental patient helps to further restrict the movement of the lower support 30.

The lower support 30 is movably interconnected with the brace assembly 46, specifically the lower brace 54, by a lower connector 42. The lower connector 42 allows for a pivoting of the lower support 30 about the axis C (e.g., a generally vertical pivoting action). Preferably the lower connector 42 is interconnected to the lower support by a ball-type joint.

Figure 1A:
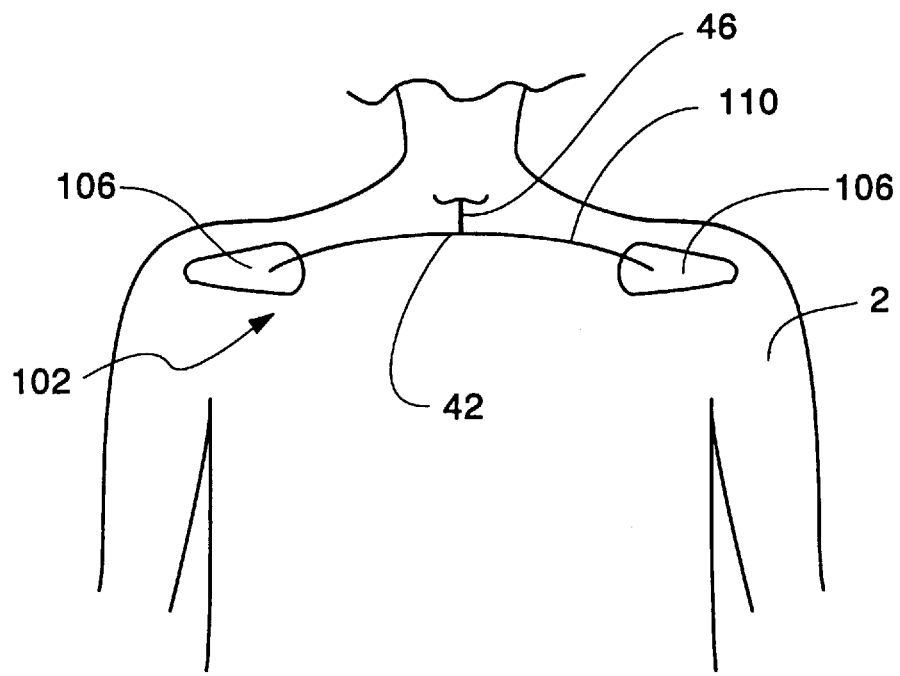
FIG. 1A is a view of another embodiment of a lower or body anchorage for the reverse pull assembly of FIG. 1.

Another embodiment of a lower support which may be used instead of the lower support 30 is illustrated in FIG. 1A. A lower support assembly 102 includes two laterally displaced clavicle engaging supports 106 which are interconnected by a lateral brace 110 and which may be appropriately secured to the dental patient 2. The clavicle engaging supports 106 may be rigidly interconnected with the lateral brace 110 or may be movable relative to the lateral brace 110 to account for certain movements by the dental patient 2. The lower portion of the brace assembly 46 may be interconnected with the lateral brace 110 in the same manner which the brace assembly 46 interconnects with the lower support 30. It should be appreciated that these principles could be applied to the upper support 14 as well (e.g., using a pair of laterally displaced head-engaging supports positioned equidistant from the vertical midline of the patient on opposite sides thereof).

The upper support 14 and the lower support 30 (or 102) can be made from any single material or combination of materials that is generally rigid and may be contoured and padded to provide a comfortable interface with the dental patient 2. Exemplary materials include, plastic, steel, wood, and combinations thereof. In one embodiment, the metal (e.g., steel) is perforated in order to be easily bendable, yet provide sufficient rigidity. In addition, these materials may be combined with a fabric, sponge, foam or other material which provide a comfortable padding. Preferably the material which contacts the dental patient 2 allows underlying skin to "breath." Such materials include reticulated foam (i.e., open cell foam), cotton, and a combination of cotton and synthetic fiber.

Figure 2:
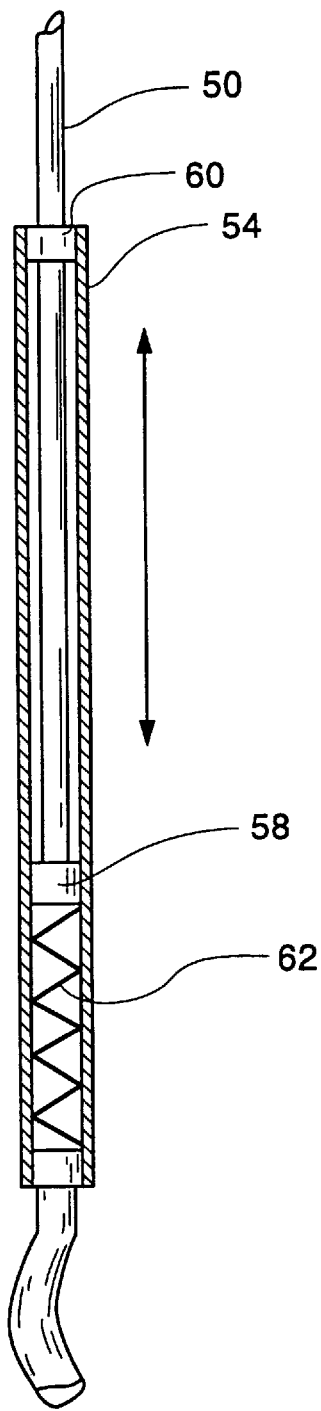
FIG. 2 is a cross-sectional view of an interconnection of lower brace and the upper brace of the brace assembly of FIG. 1.

The brace assembly 46 interconnects the upper support 14 and the lower support 30 and includes the upper brace 50 and lower brace 54. The upper brace 50 and lower brace 54 are slidably interconnected in a telescopingly-like manner which accommodates for certain movements by the dental patient 2 without adversely affecting the application of the treatment forces to the dental patient 2. As shown in FIG. 2, a stop 58 is fixedly attached to the lower end of the upper brace 50, which is received within the interior of the lower brace 54, and engages a spring 62 which is contained within the lower brace 54 and which is seated in a lower portion of the lower brace 54. The upper brace 50 may then advance further within the lower brace 54 by compressing the spring 62 and may move away from the lower brace 54 which allows for expansion of the spring 62. Moreover, the spring 62 may be sized such that it holds the weight of the assembly 10 neutrally with the head of the dental patient 2 in the level position. Preferably, the lower brace 54 does not contain the spring 62 and simply allows the upper brace 50 to slide freely within the lower brace 54. To allow relatively free movement of the upper brace 50 within the interior of the lower brace 54, the inner diameter the lower brace 54 which receives the upper brace 50 is larger than the diameter of the upper brace 50. The fitting 60 has an aperture which is slightly larger than the diameter of the upper brace 50 to allow the upper brace 50 to move vertically within the lower brace 54. An inadvertent removal of the upper brace 50 from the lower brace 54 is prevented by the stop 58 which is interconnected to the bottom of the upper brace 50 and is larger than the aperture present in the fitting 60.

Alternatively, the upper brace 50 can be interconnected to the lower brace 54 by a thread mechanism. For example, the lower portion of the upper brace 50 can have a threaded bolt proximate to its lower end, and the tube section of the lower brace 54 can have a corresponding threaded aperture to allow interconnection of the upper brace 50 to the lower brace 54. Unlike the slidable mechanism discussed above, a threaded interconnection mechanism fixes the length of the brass assembly 46 at a desired length.

Figure 1B:
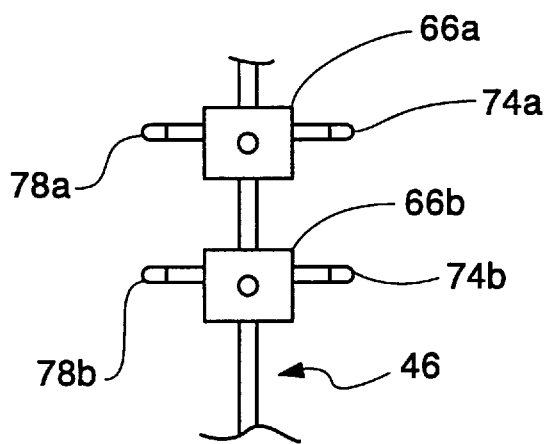
FIG. 1B is a view of another embodiment of a portion of a brace assembly for the reverse pull assembly of FIG. 1.

The brace assembly 46 also provides a mounting for the elastics 82 such that the desired generally mesially directed treatment force may be applied to the dental patient 2. In FIG. 1, the brace assembly 46 is presented in a somewhat distorted view to enhance illustration of various features. Typically, it is more desirable for the brace assembly to more closely follow the patient's profile as illustrated in FIG. 1B where the brace assembly 46' is generally about 1 inch in front of the lips of the patient 2.

Figure 1C:
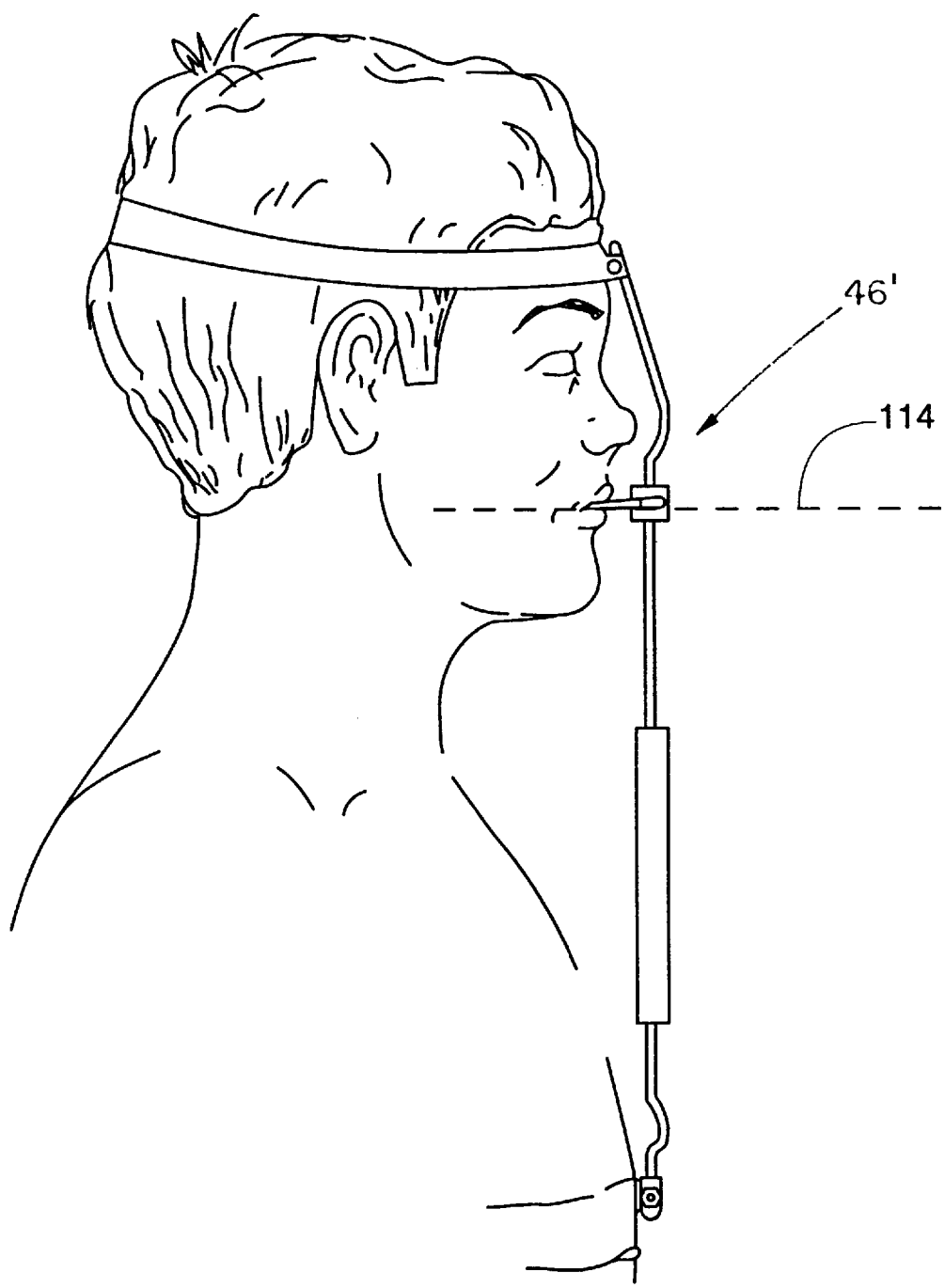
FIG. 1C is a view of another embodiment of a brace assembly for the reverse pull assembly of FIG. 1.

Referring back to FIG. 1, a mount 66 is disposed on the upper brace 50 and maintains a fixed position relative to the upper brace 50 by the engagement of a set screw 70 against the upper brace 50. The set screw 70 may engage a flat portion of the upper brace 50 which maintains the assembly 10 in the desired position. Disengagement of the set screw 70 allows the vertical positioning of the mount 66 to be adjusted relative to the upper brace 50 and thus relative to the dental patient 2. This adjustment allows the reverse pull, extraoral dental assembly 10 to be used with a variety of dental patient's having different physical characteristics and/or allows for changing the vector of the treatment force being applied to the dental patient 2 if required for treatment. For instance, in certain situations it may be desirable to apply a more "downwardly" directed force than would typically be used to treat a Class III malocclusion and the assembly 10 allows the practitioner to utilize this type of force. As a general rule, it will be desirable for the mount 66 to be adjustable between positions relative to the upper brace 50 of about ¼ inch above the line of embrasure 114 (FIG. 1C) and about ½ inch below the line of embrasure 114.

In some cases, a "downwardly" directed force generated by the assembly 10 can result in the lower support 30 being raised upward, thereby reducing the amount of a downwardly directed force. It will be appreciated that this upward movement of the lower support 30 caused by the downwardly directed force can be gradual or abrupt. In another embodiment of the present invention, FIG. 3 shows a chin stop assembly 200 interconnected to the brace assembly 46 to prevent lower support 30 from being raised upward when a downwardly directed force is applied by the apparatus of the present invention. Typically, the placement of the chin stop assembly 200 on the brace assembly 46 is adjustable to be used in a variety of applications and with a variety of dental patient's having different physical characteristics.

As shown in FIG. 3, the chin stop assembly 200 is disposed on the upper brace 50 and maintains a fixed position relative to the upper brace 50 by the engagement of a set screw 216 against the upper brace 50. The set screw 216 may engage a flat area on the upper brace 50 to maintain he chin stop assembly 200 in the desired position. Disengagement of the set screw 216 allows the vertical positioning of the chin stop assembly 200 to be adjusted relative to the upper brace 50 and allows the position of the chin stop assembly 200 on the upper brace 50 to be adjusted according to a particular physical characteristics of the dental patient to minimize or prevent the lower support 30 from moving upward. The chin stop assembly 200 can have a chin bar 204 which interconnects a chin support member 208 to the chin stop mount 212. The chin bar 204 and the chin stop mount 212 can be slidably interconnected similar to upper brace 50 and the lower brace 54 as discussed above. Alternatively, the chin bar 204 and the chin stop mount 212 can be interconnected via a threaded bolt at the end section of the chin bar 204 and a corresponding thread aperture located on the chin stop mount 212. Although the chin bar 204 can be straight, it is preferred that it be in an L-shaped form which provides a chin support without having the chin bar 204 be in contact with the patient.

The chin stop assembly 200 can further include a chin support member 208 which is generally rigid and may be contoured and/or padded to provide a comfortable interface with the dental patient's chin. Preferably, the chin support member 208 is interconnected to the chin bar 204 by a ball-type joint to allow the chin support member 208 to pivot and rotate freely. The chin support member padding can be derived from any material which provides sufficient comfort, such as cloth, foam, rubber, plastic, wood, metal, paper and any combinations thereof. It will be appreciated that although the chin stop assembly 200 can contain more than one element, the entire chin stop assembly 200 can be fabricated as a single piece or can be fabricated to include variety of pieces to allow individual tailoring of the chin stop assembly 200 to the patient's particular physical characteristic.

The surface shape of the chin support member 208 can be flat, or it can be curved to provide more comfort to the patient. Preferably, the surface of the chin support member 208 is substantially parabolic-shaped in order to substantially conform to the shape of a chin. The surface area of the chin support member 208 is generally selected to be large enough to provide a comfortable support.

The vertically adjustable mount 66 includes a first hook 74 and a second hook 78 for receiving one or more elastics 82. Each elastic 82 extends from one of the hooks 74, 78 and interfaces with the dental patient 2. In the embodiment illustrated in FIG. 1B, two vertically displaced mounts 66 are provided which may be desirable for certain types of treatments (e.g., to allow one elastic to extend from the first hook 74a of the upper mount 66a to the lower arch, one elastic to extend from the second hook 78a of the upper mount 66a to the lower arch, one elastic from the first hook 74b of the lower mount 66b to the upper arch, and one elastic from the second hook 78b of the lower mount to the upper arch).

One way in which the interface between the dental patient 2 and the assembly 10 may be established is by attaching one of the elastics 82 to a hooked appliance, such as a buccal tube, on a band attached to a molar tooth on one side of the dental patient's 2 upper arch, and attaching the other elastic 82 to a hooked appliance, such as a buccal tube, on a band attached to a molar tooth on the other side of the dental patient's 2 upper arch. In the event that the dental patient's 2 teeth of the upper arch are interconnected to all teeth within the arch by a rigid arch wire, a generally mesially directed force is applied to the dental patient's 2 upper arch by the assembly 10. Similarly, generally mesially-directed forces can be applied to the lower arch in this manner. Forces can be simultaneously applied to the upper and lower arches, and different force vectors may be used when two mounts 66 are utilized (FIG. 1B).

The assembly 10 can also be used to move anterior teeth in the dental patient's 2 upper and/or lower arch by selective joining of teeth by the archwire, or by using elastic (82) anchor points on the teeth other than molars. Other known methods of interconnecting elastics with teeth and/or methods of interconnecting the teeth for arch movement and/or movement of the dentition may be utilized than those described herein. Due to the structure of the assembly 10, it should be appreciated that it allows for simultaneous treatment of the upper arch/upper dentition and the lower arch/lower dentition (e.g., due to its stability on the dental patient 2 by using the head and body supports). In this regard, four elastics 82 may be used, two for the upper teeth/arch and two for the lower teeth/arch. The use of two vertically displaced mounts 66 may also be utilized to further augment the direction of forces. Moreover, it should be appreciated that other ways of interfacing the elastics 82 with the dental patient 2 may be utilized depending upon, for instance, the particular treatment to be used with the present invention's ability to apply generally mesially directed forces to the dental patient 2.

One particularly useful embodiment of the brace assembly 46 having a chin stop assembly 200 of the present invention is shown in FIG. 3. In this particular embodiment, the upper brace 50 is a bar (e.g., a stainless steel bar) and has a structure substantially shown in FIG. 4. As used in this invention a "bar" can be a solid bar or a hollow bar (i.e., a tube). The diameter of the bar is from about 0.08 inches to about 0.5 inches, preferably about 0.13 inches. The overall length of the upper brace 50 is from about 7 inches to about 12 inches, preferably about 9 inches. And its net length (i.e., distance 320) is from about 5 inches to about 10 inches, preferably about 7.5 inches. The upper brace 50 has a first curvature 300 with a radius of curvature of from about 0.1 inches to about 1 inches, preferably about 0.4 inches. The upper brace 50 is then curved upward creating a second curvature 336 having a radius of curvature of from about 0.4 inches to about 0.9 inches, preferably about 0.7 inches. The inclination angle 324 is from about 15° to about 30°, preferably about 22°. The radius of curvature of the third curvature 304 is from about 0.5 inches to about 1.5 inches, preferably about 0.9 inches. The length 328 is from about 0.8 inches to about 1.7 inches, preferably at about 1.4 inches. The upper brace 50 can have an angle 340 which inclines slightly from about 1° to about 10°, preferably about 5°. The length 332 is from about 2 inches to about 4 inches, preferably about 3 inches. The third curvature 304 results in a declination angle 312 of from about 40° to about 50°, preferably about 46°. The radius of curvature of the third curvature 304 is from about 0.6 inches to about 1.3 inches, preferably about 0.9 inches. The upper brace 50 also contains a fourth curvature 316 which has a radius of curvature of from about 0.4 inches to about 0.9 inches, preferably about 0.7 inches. The length 344 of the upper brace 50 is from about 3.5 inches to about 5.5 inches, preferably about 5 inches.

Referring again to FIG. 3, the upper connector 26 can be attached to the top of the upper brace 50 by a thread mechanism. For example, the top portion of the upper brace 50 can be threaded of about 0.2 inches to about 0.8 inches, preferably for about 0.5 inches. The upper connector 26 is interconnect to the upper brace 50 by having a threaded aperture to securely connect the upper connector 26 to the upper brace 50. The upper connector 26 is then interconnected to the upper support 14 by a ball-type joint to allow the upper support 14 to pivot and/or rotate freely. For added comfort, the upper support 14 can include a padding material that is from about ⅟₃₂ inches to about ½ inches thick, preferably about ⅛ inches.

The tube section 250 of the lower brace 54 has a length of about 2 inches to about 4 inches, preferably about 3.2 inches. It has a diameter of about 0.08 inches to about 0.25 inches, preferably about 0.13 inches. The upper brace 50 is slidably interconnected to the tube section 250 as discussed above. The lower support bar 254 on the lower brace 54 is interconnected to the tube section 250 by a thread mechanism. It should be appreciated that the tube 250 and the lower support bar 254 can be a single-piece rather than two separate elements.

Figure 5:
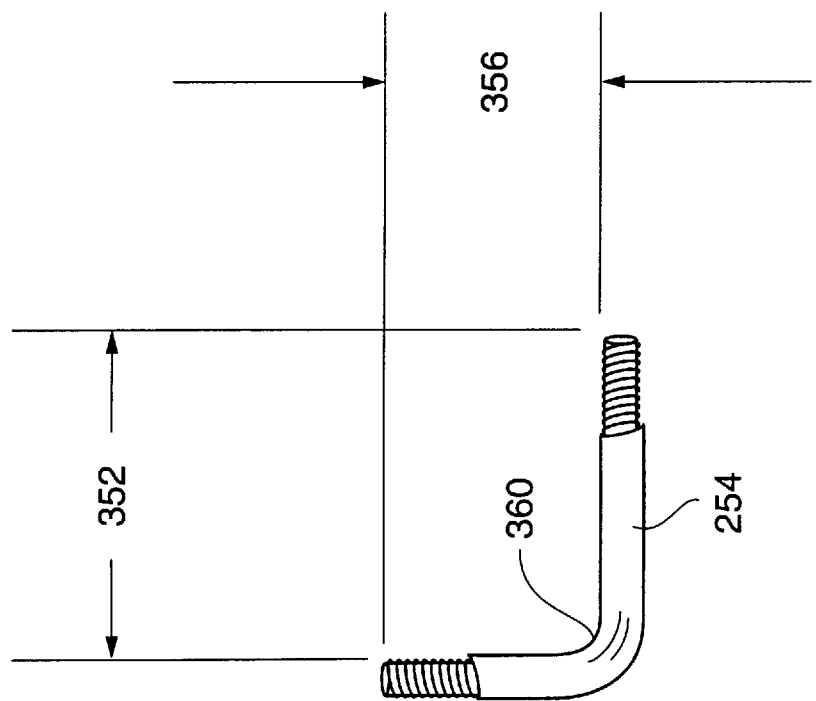
FIG. 5 is a detailed view of the lower support bar 254.

As shown in FIG. 5, the lower support bar 254 can be a stainless steel bar having a curvature that is substantially a right angle with a radius of curvature 360 of from about 0.2 inches to about 0.7 inches, preferably about 0.4 inches. Its length 352 is from about 1 inch to about 2 inches, preferably about 1.5 inches. Its height 356 is from about 0.5 inches to about 1.5 inches, preferably about 0.9 inches. It is threaded on the both ends which allows it to be interconnected to the tube 250 and the lower connector 42 by a thread mechanism.

The lower connector 42 is from about 0.5 inches to about 1.2 inches, preferably about 0.8 inches. The lower connector 42 is interconnected with the lower support 30 by a ball-type joint to allow the lower support 30 to pivot and/or rotate freely.

The chin stop assembly 200 can be interconnected to the upper brace 50 by the chin stop mount 212. The chin bar 204 and the chin stop mount 212 can be a single piece or they can be a separate unit which is interconnected to provides a restraining means to prevent movement of the chin bar 204 relative to the chin stop mount 212. Preferably the chin bar 204 and the chin It has a diameter of about 0.08 inches to about 0.25 inches, preferably about 0.13 inches. The upper brace 50 is slidably interconnected to the tube section 250 as discussed above. The lower support bar 254 on the lower brace 54 is interconnected to the tube section 250 by a thread mechanism. It should be appreciated that the tube 250 and the lower support bar 254 can be a single-piece rather than two separate elements.

As shown in FIG. 5, the lower support bar 254 can be a stainless steel bar having a curvature that is substantially a right angle with a radius of curvature 360 of from about 0.2 inches to about 0.7 inches, preferably about 0.4 inches. Its length 352 is from about 1 inch to about 2 inches, preferably about 1.5 inches. Its height 356 is from about 0.5 inches to about 1.5 inches, preferably about 0.9 inches. It is threaded on the both ends which allows it to be interconnected to the tube 250 and the lower connector 42 by a thread mechanism.

The lower connector 42 is from about 0.5 inches to about 1.2 inches, preferably about 0.8 inches. The lower connector 42 is interconnected with the lower support 30 by a ball-type joint to allow the lower support 30 to pivot and/or rotate freely.

The chin stop assembly 200 can be interconnected to the upper brace 50 by the chin stop mount 212. The chin bar 204 and the chin stop mount 212 can be a single piece or they can be a separate unit which is interconnected to provides a restraining means to prevent movement of the chin bar 204 relative to the chin stop mount 212. Preferably the chin bar 204 and the chin stop mount 212 are separate units which are interconnected by a thread mechanism or a slidably connecting mechanism similar to the interconnection between the upper brace 50 and the lower brace 54. The chin stop mount 212 can be a threaded stainless steel tube having an inner diameter of from about 0.1 inches to about 0.5 inches, preferably about 0.2 inches. The outer diameter of the chin stop mount 212 is from about 0.1 inches to about 0.7 inches, preferably about 0.3 inches. The length of the chin stop mount 212 is from about 0.4 inches to about 1.2 inches, preferably about 0.8 inches. The chin stop mount 212 is interconnected to the upper brace 50 by a set screw 216 which positions the Chin stop mount 212 to the upper brace 50 at a desired position.

Figure 6:
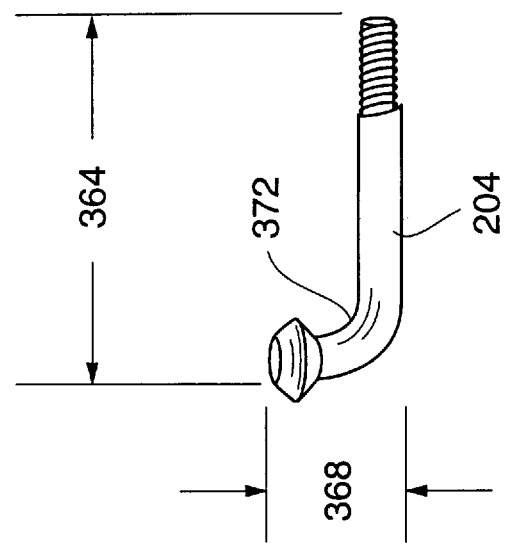
FIG. 6 is a detailed view of the chin bar 204.

As shown in detail in FIG. 6, the chin bar 204 can be a stainless steel bar having a substantially a right angle bend near where it is connected to a chin support member 208 (see FIG. 3). The length 364 of the chin bar 204 is from about 1.2 inches to about 2 inches, preferably about 1.6 inches. Its height 368 is from about 0.1 inches to about 0.5 inches, preferably about 0.3 inches. The radius of curvature 372 is from about 0.1 inches to about 0.3 inches, preferably about 0.2 inches.

The chin support member 208 can be a stainless steel plate having a thickness of from about 0.01 inches to about 0.1 inches, preferably about 0.02 inches. Preferably, it is about 2 inches to about 4 inches long, and more preferably about 2.8 inches. Preferably, its width is from about 0.5 inches to about 1.5 inches, more preferably about 1 inch. The chin support member 208 can also comprise a chin support member pad for additional comfort.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A reverse-pull, extraoral dental assembly, comprising:
    first means for engaging a portion of a dental patient's head;
    second means for engaging a portion of the dental patient's body spaced from the patient's head;
    third means for interconnecting said first and said second means for engaging, said third means being generally displaced outwardly from the frontal region of the dental patient;
    fourth means, interconnectable with said third means, for anchoring a means for exerting at least a mesially directed force on at least one of the patient's lower jaw, the patient's maxilla, and a tooth of the patient; and
    fifth means, interconnectable with said first means, for preventing upward movement of said assembly by providing a counterforce to any downwardly directed mesial force exerted by said fourth means.

2. The assembly of claim 1, wherein said first means comprises means for engaging at least a portion of a forehead of said dental patient.

3. The assembly of claim 1, wherein said first means comprises at least one forehead support.

4. The assembly of claim 1, wherein said second means comprises means for engaging at least a frontal portion of a body of said dental patient.

5. The assembly of claim 1, wherein said second means comprises means for engaging a sternum region of said dental patient.

6. The assembly of claim 5, wherein said second means comprises a lower support.

7. The assembly of claim 1, wherein said third means comprises a substantially rigid brace assembly.

8. The assembly of claim 7, wherein at least a portion of said brace assembly is generally arcuately shaped.

9. The assembly of claim 7, wherein at least a portion of said brace assembly is displaced generally outwardly away from said dental patient.

10. The assembly of claim 7, wherein said brace assembly is pivotally interconnected with each of said first and second means for engaging.

11. The assembly of claim 7, wherein said brace assembly comprises an upper brace and a lower brace, said upper and lower braces being telescopically interconnected to provide a telescoping action between said upper and lower braces during dental patient movement.

12. The assembly of claim 1, wherein said third means is disposed within a reference plane which extends through a nose of the dental patient to generally bisect a dental patient's head into mirrored images.

13. The assembly of claim 1, wherein said fourth means is rigidly interconnected with said third means.

14. The assembly of claim 1, wherein said fifth means comprises a chin bar, a chin stop support member and a chin stop mount.

15. The assembly of claim 14, wherein said chin bar is substantially L-shaped.

16. The assembly of claim 14, wherein said chin bar is rigidly interconnected with said third means.

17. The assembly of claim 14, further comprising means for adjusting said chin bar relative to said chin stop support member.

18. The assembly of claim 14, wherein said chin bar and chin stop mount is telescopically interconnected to provide a telescoping action between said chin bar and chin stop mount during dental patient movement.

19. The assembly of claim 1, further comprising means for adjusting a vertical position of said fourth means relative to said third means.

20. An assembly of claim 1, wherein said fourth means is slidably interconnected with said third means.

21. The assembly of claim 1, further comprising means for adjusting a vertical position of said fifth means relative to said third means.

22. The assembly of claim 1, wherein said fifth means is slidably interconnected with said third means.

23. A reversible, extra-oral dental assembly comprising:
    a first frontal support engageable with at least a portion of a forehead of a dental patient;
    a second frontal support adapted to be engaged with a portion of the patient's body spaced from the patient's head;
    a chin stop assembly adapted to be engaged with a portion of the patient's chin;
    a brace assembly extending between and interconnected with each of said first and second frontal supports and said chin stop; and
    a treatment force transfer member mounting interconnected with said brace assembly for applying a force to at least one of the patient's lower jaw, the patient's maxilla, and a tooth of the dental patient.

24. The assembly of claim 23, wherein at least a portion of said brace assembly is generally arcuately shaped.

25. The assembly of claim 23, wherein at least a portion of said brace assembly extends generally mesially away from the dental patient.

26. The assembly of claim 23, wherein said chin stop assembly comprises a chin bar and a chin stop support member.

27. The assembly of claim 23, further comprising means for adjusting a vertical position of said chin stop assembly relative to said brace assembly.

28. The assembly of claim 23, wherein the length of said chin bar is slidably adjustable.

29. A method of orthopedic and/or orthodontic treatment comprising:
    engaging a frontal head region of a dental patient outside of a jaw region of the dental patient;
    engaging a frontal body region of the dental patient spaced from the head of the dental patient;
    engaging the chin of the dental patient;
    exerting at least a downwardly directed force on at least one of the dental patient's lower jaw, the dental patient's maxilla, and a tooth of the dental patient; and
    exerting generally distally directed forces on said frontal head region and said frontal body region.

* * * * *